United States Patent
Buil et al.

(10) Patent No.: US 12,035,978 B2
(45) Date of Patent: Jul. 16, 2024

(54) METHOD OF DETERMINING A POSITION AND/OR ORIENTATION OF A HAND-HELD DEVICE WITH RESPECT TO A SUBJECT, A CORRESPONDING APPARATUS AND A COMPUTER PROGRAM PRODUCT

(71) Applicant: KONINKLIJKE PHILIPS N.V., Eindhoven (NL)

(72) Inventors: Vincentius Paulus Buil, Veldhoven (NL); Lucas Jacobus Franciscus Geurts, Sterksel (NL); Martin Jurna, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 428 days.

(21) Appl. No.: 17/312,972

(22) PCT Filed: Jan. 22, 2020

(86) PCT No.: PCT/EP2020/051461
§ 371 (c)(1),
(2) Date: Jun. 11, 2021

(87) PCT Pub. No.: WO2020/152196
PCT Pub. Date: Jul. 30, 2020

(65) Prior Publication Data
US 2022/0047333 A1    Feb. 17, 2022

(30) Foreign Application Priority Data
Jan. 24, 2019  (EP) .................................... 19153523

(51) Int. Cl.
*A61B 34/20* (2016.01)
*A61B 18/20* (2006.01)
(Continued)

(52) U.S. Cl.
CPC ............ *A61B 34/20* (2016.02); *A61B 18/203* (2013.01); *G06T 7/73* (2017.01);
(Continued)

(58) Field of Classification Search
CPC ........ A61B 18/203; A61B 2017/00752; A61B 2018/0047; A61B 2018/00476;
(Continued)

(56) References Cited

U.S. PATENT DOCUMENTS

2002/0173781 A1   11/2002  Cense
2007/0005047 A1    1/2007  Ferren
(Continued)

FOREIGN PATENT DOCUMENTS

WO   2016/071325 A1    5/2016
WO   2017/223120 A1   12/2017
WO   2018/002004 A1    1/2018

OTHER PUBLICATIONS

International Search Report and Written Opinion Dated Feb. 24, 2020 For International Application No. PCT/EP2020/051461 Filed Jan. 22, 2020.
(Continued)

*Primary Examiner* — Michael T Rozanski (57) ABSTRACT

According to an aspect, there is provided a method of determining a position and/or orientation of a hand-held device with respect to a subject. The hand-held device is for use on a body of the subject. The method comprises receiving (101) images from an imaging unit arranged in or on the hand-held device; receiving (103) a displacement signal from a displacement sensor that is arranged in or on the hand-held device to measure displacement of the hand-held device along the body when the hand-held device is in contact with the body; processing (105) the received images to determine whether a body part of the subject can be
(Continued)

identified in the received images; determining (107) whether the hand-held device is in contact with the body; determining (109) a mode of operation to use to determine a position and/or orientation of the hand-held device based on whether a body part can be identified and whether the hand-held device is in contact with the body; wherein the mode of operation to use is determined as (i) a first mode when a body part can be identified, (ii) a second mode when a body part cannot be identified and the hand-held device is not in contact with the body, and (iii) a third mode when the hand-held device is in contact with the body; and determining (111) the position and/or orientation of the hand-held device with respect to the body of the subject using the received images and/or received displacement signal according to the determined mode of operation.

17 Claims, 5 Drawing Sheets

(51) Int. Cl.
　　　*G06T 7/73*　　　(2017.01)
　　　*A61B 18/00*　　　(2006.01)
(52) U.S. Cl.
　　　CPC .............. *A61B 2018/00476* (2013.01); *A61B 2034/2055* (2016.02); *A61B 2034/2065* (2016.02); *G06T 2207/30088* (2013.01); *G06T 2207/30196* (2013.01); *G06T 2207/30244* (2013.01)

(58) Field of Classification Search
　　　CPC .......... A61B 2018/00648; A61B 2018/00785; A61B 2018/00904; A61B 2018/1807; A61B 2034/2055; A61B 2034/2065; A61B 2090/065; A61B 2090/067; A61B 2090/0818; A61B 34/20; A61B 8/4254; A61N 2005/0626; A61N 2005/0644; A61N 5/0616; A61N 5/0622; A61N 5/067; G06T 2207/10028; G06T 2207/10132; G06T 2207/30088; G06T 2207/30196; G06T 2207/30204; G06T 2207/30244; G06T 7/73
　　　See application file for complete search history.

(56) References Cited

U.S. PATENT DOCUMENTS

| | | |
|---|---|---|
| 2008/0107305 A1 | 5/2008 | Vanderkooy |
| 2013/0296670 A1 | 11/2013 | Chen |
| 2013/0296707 A1 | 11/2013 | Anthony |
| 2015/0182757 A1 | 7/2015 | Levine |
| 2019/0375121 A1 | 12/2019 | Palero |

OTHER PUBLICATIONS https://en.wikipedia.org/wiki/Visual_odometry.
https://en.wikipedia.org/wiki/Dead_reckoning.
Banchev, et al: "Comparison of pixel based skin recognition techniques", 2012.

METHOD OF DETERMINING A POSITION AND/OR ORIENTATION OF A HAND-HELD DEVICE WITH RESPECT TO A SUBJECT, A CORRESPONDING APPARATUS AND A COMPUTER PROGRAM PRODUCT

CROSS REFERENCE TO RELATED APPLICATIONS

This application is the U.S. National Phase application under 35 U.S.C. § 371 of International Application No. PCT/EP2020/051461 filed Jan. 22, 2020, which claims the benefit of European Patent Application Number 19153523.6 filed Jan. 24, 2019. These applications are hereby incorporated by reference herein.

FIELD OF THE INVENTION

This disclosure relates to a hand-held device that is for use on a body of a subject, and in particular to a technique for determining a position and/or orientation of the hand-held device with respect to the subject, for example as the hand-held device is moved towards and on to the body of the subject.

BACKGROUND OF THE INVENTION

Many types of hand-held device are available that can be used on a body of a subject to provide a treatment operation to the body or a personal care operation on the body. For example, there are hand-held devices for the removal of unwanted hairs using various techniques such as shaving, electrolysis, plucking, laser and light therapies (known as photoepilation or Intense Pulsed Light, IPL) and injection of therapeutic anti-androgens. Other types of dermatological treatments, including hair growth reduction and treating acne, can also use light-based technologies. Hand-held devices can also be used for providing a massage to the subject, for providing a nail treatment, for providing physiotherapy, for applying patches to the subject (e.g. electrocardiogram electrodes, etc.). Another type of hand-held device is an ultrasound probe.

For example, IPL treatment is characterized by the user of the IPL device treating relatively small spots of the skin for the purpose of permanent hair removal. A problem with this treatment is that the user does not receive (visual) feedback about which area they have treated already. This can result in untreated areas or double treated areas. The recommended procedure for IPL treatment is that the user treats a body part in consecutive lanes or circles. In the case of lower leg treatment in consecutive lanes, for example, the user is recommended to position the IPL device underneath the knee and step-by-step go downwards to the ankle, lift the device, place it underneath the knee in the next lane, go downwards, and so on. In the case of lower leg treatment in circles, for example, the user is recommended to step-by-step go around the leg, place the device on the next circle downwards, go around the leg again, and so on.

However, the user may pause during the procedure, for example if they are distracted or if they temporarily put away the device, and continue the treatment later. This is challenging since the user needs to remember which parts of the body have been treated and where the treatment should be continued from.

Therefore, when using an IPL device, or other types of hand-held devices, it can be useful for the position and/or orientation of the hand-held device with respect to the body to be determined automatically. This position and/or orientation information can be used for various purposes, including by the user in determining where to resume an operation on the body.

SUMMARY OF THE INVENTION

To support users in correctly positioning and/or orientating a device during treatment, different approaches have been explored, including solutions enabled by device localization. Some examples use skin mapping with an optical sensor inside the device (which can be enabled by storing skin patterns and skin speed/distance sensing), for example as described in WO 2016/071325. Other examples use device-to-body part mapping with an external camera (which can be enabled by the camera viewing a body part and the IPL device, and using skeleton recognition and device orientation recognition to position the device with respect to the body).

Navigation or positioning of a device using skin mapping requires the building up and retrieval of locations in a skin map, in which it is necessary to know where certain skin patches are in relation to the body part. As such, an extra reference point is needed, which could be provided via an external camera (i.e. not on the device). When the map has been created, the user can randomly position the device at a skin location, and based on the map the device can know the location in relation to the body part. However, the disadvantages of this approach are that it requires quite some computing power, which is typically not available in hand-held devices, and it requires an initial skin mapping procedure to be performed by the user.

It is considered that obtaining relative positioning can be sufficient if other means are available to get an absolute position reference. Device-to-body part mapping with an external camera can offer this information. However, an external camera requires a line of sight from the camera to the body part and the device, and a fixed camera position (e.g. on a stand) will not always have the required line of sight. Requiring the user to hold the camera in their hand will result in awkward ergonomics, e.g. both hands are required to hold a device, so no hand is left to support themselves while doing the treatment.

Therefore, there is a need for improvements in the way in which a position and/or orientation of a hand-held device with respect to the body of a subject is determined that overcomes one or more of the problems associated with the above techniques.

According to a first specific aspect, there is provided a method of determining a position and/or orientation of a hand-held device with respect to a subject. The hand-held device is for use on a body of the subject. The method comprises receiving images from an imaging unit, wherein the imaging unit is arranged in or on the hand-held device; receiving a displacement signal from a displacement sensor, wherein the displacement sensor is arranged in or on the hand-held device to measure displacement of the hand-held device along the body when the hand-held device is in contact with the body; processing the received images to determine whether a body part of the subject can be identified in the received images; determining whether the hand-held device is in contact with the body; determining a mode of operation to use to determine a position and/or orientation of the hand-held device based on whether a body part can be identified and whether the hand-held device is in contact with the body; wherein the mode of operation to use is determined as (i) a first mode when a body part can be identified, (ii) a second mode when a body part cannot be identified and the hand-held device is not in contact with the body, and (iii) a third mode when the hand-held device is in contact with the body; and determining the position and/or orientation of the hand-held device with respect to the body of the subject using the received images and/or received displacement signal according to the determined mode of operation. When operating in the first mode, the step of determining the position and/or orientation of the hand-held device comprises processing the received images to determine a first position and/or first orientation of the hand-held device with respect to the identified body part. When operating in the second mode, the step of determining the position and/or orientation of the hand-held device comprises processing the received images to determine an amount of movement of the hand-held device from the determined first position and/or an amount of change in the orientation of the hand-held device from the determined first orientation, and determining a second position of the hand-held device with respect to the identified body part from the determined first position and the determined amount of movement and/or determining a second orientation of the hand-held device with respect to the identified body part from the determined first orientation and the determined amount of change. When operating in the third mode, the step of determining the position and/or orientation of the hand-held device comprises processing the received displacement signal to determine an amount of displacement of the hand-held device along the body from the determined second position, and determining a third position of the hand-held device with respect to the identified body part from the determined second position and the determined amount of displacement. Thus, the first aspect provides for an improved way to determine a position and/or orientation of a hand-held device with respect to the body of a subject using a displacement sensor and imaging unit that are on or in the hand-held device, and the position and/or orientation can be determined both when the hand-held device is spaced from the body and when the hand-held device is in contact with the body.

In some embodiments, if the position and/or orientation of the hand-held device is determined using the first mode, the method further comprises: if a body part can be identified in further received images, continuing to operate in the first mode to determine the position and/or orientation of the hand-held device with respect to the body using the further received images; and if a body part cannot be identified in the further received images, operating in the second mode to determine the position and/or orientation of the hand-held device with respect to the body using the further received images.

In some embodiments, if the position and/or orientation of the hand-held device is determined using the second mode, the method further comprises: if a body part cannot be identified in further received images and the hand-held device is not in contact with the body, continuing to operate in the second mode to determine the position and/or orientation of the hand-held device with respect to the body using the further received images; if a body part can be identified in the further received images, operating in the first mode to determine the position and/or orientation of the hand-held device with respect to the body using the further received images; and if the hand-held device is in contact with the body, operating in the third mode to determine the position and/or orientation of the hand-held device with respect to the body using a further received displacement signal.

In some embodiments, if the position and/or orientation of the hand-held device is determined using the third mode, the method further comprises: if the hand-held device is in contact with the body, continuing to operate in the third mode to determine the position and/or orientation of the hand-held device with respect to the body using a further received displacement signal; if the hand-held device is not in contact with the body and a body part cannot be identified in further received images, operating in the second mode to determine the position and/or orientation of the hand-held device with respect to the body using the further received images; and if the hand-held device is not in contact with the body and a body part can be identified in the further received images, operating in the first mode to determine the position and/or orientation of the hand-held device with respect to the body using the further received images.

In some embodiments, when operating in the second mode, the second position is determined from a last first position determined when last operating in the first mode and/or the second orientation is determined from a last first orientation determined when last operating in the first mode.

In some embodiments, when operating in the third mode, the third position is determined from a last second position determined when last operating in the second mode.

In some embodiments, when operating in the third mode, the step of determining the orientation comprises processing subsequent images received from the imaging unit in order to determine a change in orientation from an image transformation between the subsequent images and determining a third orientation of the hand-held device with respect to the identified body part from the determined second orientation and the determined amount of change. For example, if the user rotates the hand-held device around the axis perpendicular to the skin, then the image captured by the imaging unit will rotate. If the user rotates the hand-held device around another axis, the image captured by the imaging unit will deform to a trapezoid shape.

In some embodiments, the step of determining whether the hand-held device is in contact with the body comprises: receiving a contact signal from a body contact sensor; and processing the contact signal to determine whether the hand-held device is in contact with the body. The use of a body contact sensor enables the change to the third mode to occur (and thus for the displacement signal to be used) as soon as the hand-held device is in contact with the body.

In some embodiments, the step of determining whether the hand-held device is in contact with the body comprises determining whether the hand-held device is in contact with the body by analysing the received images. This embodiment has an advantage that a separate body contact sensor is not required.

In some embodiments, the step of determining whether the hand-held device is in contact with the body comprises determining whether the hand-held device is in contact with the body by analysing the received displacement signal. This embodiment has an advantage that a separate body contact sensor is not required.

In some embodiments, the method further comprises controlling or adjusting control of the hand-held device based on the determined third position.

In some embodiments, the method further comprises outputting guidance to a user of the hand-held device based on the determined first position and/or first orientation, the determined second position and/or second orientation, and/or the determined third position.

According to a second aspect, there is provided a computer program product comprising a computer readable medium having computer readable code embodied therein, the computer readable code being configured such that, on execution by a suitable processing unit or control unit, the processing unit or control unit is caused to perform the method according to the first aspect or any embodiment thereof.

According to a third aspect, there is provided an apparatus for use in determining a position and/or orientation of a hand-held device with respect to a subject. The hand-held device comprises an imaging unit that is arranged in or on the hand-held device and that obtains images, and a displacement sensor that is arranged in or on the hand-held device to measure displacement of the hand-held device along the body when the hand-held device is in contact with the body. The apparatus comprises a processing unit or a control unit configured to perform the method according to the first aspect or any embodiment thereof. Thus, the third aspect provides an apparatus that uses an improved way to determine a position and/or orientation of a hand-held device with respect to the body of a subject using a displacement sensor and imaging unit that are on or in the hand-held device, and the position and/or orientation can be determined both when the hand-held device is spaced from the body and when the hand-held device is in contact with the body.

In some embodiments, the hand-held device comprises a treatment head portion for performing a treatment operation on the body of the subject.

In some embodiments, the apparatus is the hand-held device. These embodiments have the advantage that a separate apparatus is not required.

In some embodiments, the processing unit or control unit is configured to receiving images from the imaging unit; receive a displacement signal from the displacement sensor; process the received images to determine whether a body part of the subject can be identified in the received images; determine whether the hand-held device is in contact with the body; determine a mode of operation to use to determine a position and/or orientation of the hand-held device based on whether a body part can be identified and whether the hand-held device is in contact with the body; wherein the mode of operation to use is determined as (i) a first mode when a body part can be identified, (ii) a second mode when a body part cannot be identified and the hand-held device is not in contact with the body, and (iii) a third mode when the hand-held device is in contact with the body; and determine the position and/or orientation of the hand-held device with respect to the body of the subject using the received images and/or received displacement signal according to the determined mode of operation. When operating in the first mode, the processing unit or control unit is configured to determine the position and/or orientation of the hand-held device by processing the received images to determine a first position and/or first orientation of the hand-held device with respect to the identified body part. When operating in the second mode, the processing unit or control unit is configured to determine the position and/or orientation of the hand-held device by processing the received images to determine an amount of movement of the hand-held device from the determined first position and/or an amount of change in the orientation of the hand-held device from the determined first orientation, and determining a second position of the hand-held device with respect to the identified body part from the determined first position and the determined amount of movement and/or determining a second orientation of the hand-held device with respect to the identified body part from the determined first orientation and the determined amount of change. When operating in the third mode, the processing unit or control unit is configured to determine the position and/or orientation of the hand-held device by processing the received displacement signal to determine an amount of displacement of the hand-held device along the body from the determined second position, and determining a third position of the hand-held device with respect to the identified body part from the determined second position and the determined amount of displacement.

According to a fourth aspect, there is provided a system for use in determining a position and/or orientation of a hand-held device with respect to a subject, the system comprising: a hand-held device that comprises an imaging unit arranged in or on the hand-held device and a displacement sensor arranged in or on the hand-held device; and an apparatus according to the third aspect or any embodiment thereof.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

Figure 1:
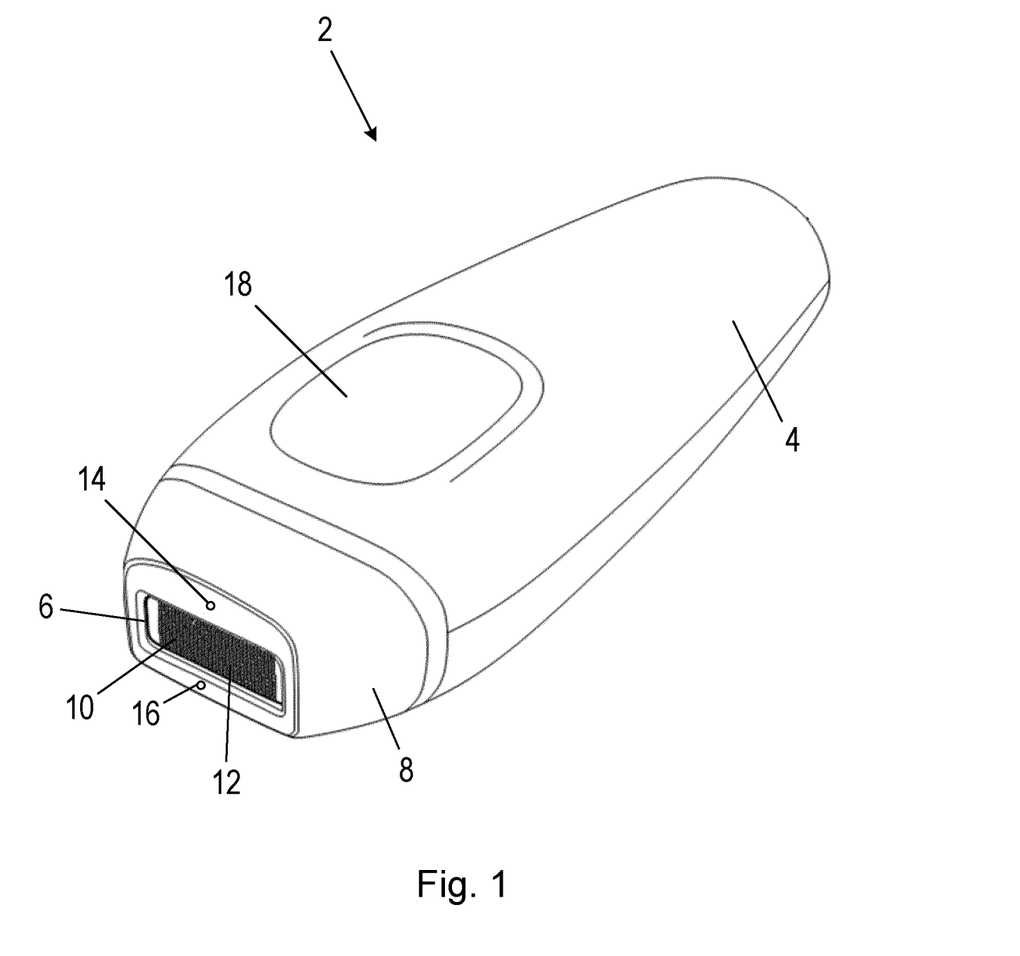
FIG. 1 is an illustration of an exemplary hand-held device.

FIG. 1 is an illustration of an exemplary hand-held device 2. The techniques described herein can be used to determine the position and/or orientation of the hand-held device 2 relative to a body part of a subject. The handheld device 2 is for use on a body of a subject (e.g. a person or an animal), and is to be held in one or both hands of a user during use. The hand-held device 2 is to perform some operation on the body of the subject, when the hand-held device 2 is in contact with the body of the subject. In some embodiments, the hand-held device 2 is to perform some operation on the skin of the subject. In some embodiments, the hand-held device 2 can perform the operation on the skin or body of the subject through the clothing of the subject (i.e. the hand-held device 2 can be in contact with the skin or body via the subject's clothing), and, where possible, references herein to contact with the body or skin should be understood as including, or potentially including, contact with the body or skin via one or more layers of clothing).

As described herein, the hand-held device 2 is operated or used by a 'user', and the hand-held device 2 is used on a body of a 'subject'. In some cases the user and the subject is the same person, i.e. the hand-held device 2 is held in a hand and used by a user on themselves (e.g. used on the skin on their leg). In other cases the user and the subject are different people, e.g. the hand-held device 2 is held in a hand and used by a user on someone else.

The hand-held device 2 comprises a housing 4 that includes a head portion 6 at one end 8 of the body 4 (referred to herein as the 'head end' of the hand-held device 2, which is the end of the hand-held device 2 that is to be placed into contact with the subject). The head portion 6 is to be placed on the body of the subject and performs an operation on the body or skin of the subject, at the position that the head portion 6 is in contact with the body or skin (or clothing).

In some embodiments the hand-held device 2 is for performing a treatment operation or a personal care operation on the body, the head portion 6 can be referred to as a 'treatment head portion 6', and the treatment head portion 6 will include suitable components for enabling a particular treatment or personal care operation to be performed on the body or skin, when the treatment head portion 6 is in contact with the body or skin.

The hand-held device 2 can be for performing a treatment operation or a personal care operation on the body of the subject. Some exemplary treatment operations or a personal care operations include, but are not limited to, the removal of unwanted hairs by any of shaving, electrolysis, plucking, laser and light therapies (known as photoepilation or Intense Pulsed Light, IPL) and injection of therapeutic anti-androgens; a dermatological (skin) treatment, including hair growth reduction, treating acne, a phototherapy treatment, skin rejuvenation, skin tightening, or port-wine stain treatment; pain relief; providing a massage; providing a nail treatment; and providing physiotherapy. The hand-held device 2 could alternatively be for applying patches to the body of the subject (e.g. electrocardiogram (ECG) electrodes, etc.), or the hand-held device 2 could be an ultrasound probe (e.g. for ultrasound imaging).

In the embodiment illustrated in FIG. 1, the hand-held device 2 is for performing an operation using energy or energy pulses (e.g. light or light pulses). Thus, in FIG. 1 the head portion 6 comprises an aperture 10 is arranged in or on the housing 4 so that the aperture 10 can be placed adjacent to or on (i.e. in contact with) the skin (or clothing) of the subject. The hand-held device 2 includes one or more energy sources 12 that are for generating energy pulses that are to be applied to the skin of the subject via the aperture 10 and effect a treatment operation. The one or more energy sources 12 are arranged in the housing 4 so that the energy pulses are provided from the one or more energy sources 12 through the aperture 10. The aperture 10 may be in the form of an opening at one end of the housing 4, or it may be in the form of a window (including a waveguide) that is transparent or semi-transparent to the energy pulses (i.e. the energy pulses can pass through the window).

In the exemplary embodiment shown in FIG. 1, the aperture 10 has a generally rectangular shape, which results in a generally rectangular-shaped skin treatment region on the skin. It will be appreciated that the aperture 10 can have any other desired shape. For example the aperture 10 can be square, elliptical, circular, or any other polygonal shape.

The one or more energy sources 12 can generate any suitable type of energy for performing a treatment operation, for example light, sound, radio frequency (RF) signals, microwave radiation and plasma. In the case of an energy source 12 that generates light, the energy source 12 can be configured to generate a light pulse at any suitable or desired wavelength (or range of wavelengths) and/or intensities. For example, the energy source 12 can generate visible light, infra-red (IR) light and/or ultraviolet (UV) light. Each energy source 12 can comprise any suitable type of light source, such as one or more light emitting diodes (LEDs), a (Xenon) flash lamp, a laser or lasers, etc. In a preferred embodiment, the handheld device 2 is for performing photoepilation, and the energy source(s) 12 are to provide intense light pulses. In the case of an energy source 12 that generates sound, the energy source 12 can be configured to generate a sound pulse at any suitable or desired wavelength (or range of wavelengths) and/or intensities. For example, the energy source 12 can be an ultrasound transducer.

The one or more energy sources 8 is configured to provide pulses of energy. That is, the energy source(s) 8 are configured to generate energy at a high intensity for a short duration (e.g. less than 1 second). The intensity of the energy pulse should be high enough to effect the treatment operation on the skin adjacent the aperture 10.

Of course, although the embodiment illustrated in FIG. 1 is a hand-held device 2 for performing an operation using energy or energy pulses, it will be appreciated that the head portion 6 can be configured to provide or perform other types of operations. For example, the hand-held device 2 can be a shaver or hair clippers, in which case the head portion 6 can comprise one or more cutting blades or foils for enabling hair to be cut when the head portion 6 is in contact with skin. As another example, the hand-held device 2 can be an ultrasound probe that is used to obtain ultrasound images. In this example, the head portion 6 can include an ultrasound transducer for generating ultrasound waves, and an ultrasound receiver for receiving the ultrasound waves reflected back from the inside of the body.

In accordance with the techniques described herein, to enable the position and/or orientation of the hand-held device 2 with respect to the body of the subject to be determined, the hand-held device 2 comprises an imaging unit 14 and a displacement sensor 16.

The imaging unit 14 is arranged in or on the hand-held device 2 and obtains a series of images. As described in more detail below, the images from the imaging unit 14 are to be processed to determine whether a body part of the subject can be identified in the received images. The imaging unit 14 can therefore be in any suitable position or location in or on the hand-held device 2 that enables images to be obtained that may include identifiable body parts when the hand-held device 2 is in use (e.g. when a user is moving the hand-held device 2 towards a subject). For example, in the embodiment illustrated in FIG. 1, the imaging unit 14 is arranged on the head portion 6, close to and generally planar with the aperture 10, so that the imaging unit 14 will be very close to or in contact with the subject when the head portion 6 is in contact with the subject. Alternatively, the imaging unit 14 can be arranged on the housing 4 of the hand-held device 2 so that the imaging unit 14 remains spaced from the subject, even when the head portion 6 is in contact with the subject. In this case the imaging unit 14 may face a direction in which the body of the subject will typically be when the hand-held device 2 is in use (e.g. the imaging unit 14 can face a direction in which the operation is performed by the head portion 6). With either of these arrangements of the imaging unit 14, the imaging unit 14 may be generally facing the subject as the hand-held device 2 is moved towards the subject at the start or resumption of an operation (or when the hand-held device 2 is lifted off of the body and repositioned on the subject during the operation), enabling images to be obtained that could include identifiable body parts.

In some embodiments, the imaging unit 14 is arranged or oriented on the hand-held device 2 such that a field-of-view of the imaging unit 14 includes a direction in which the head portion 6 performs the operation (e.g. a direction in which energy is emitted through the aperture 10). However, it will be appreciated that this arrangement or orientation of the imaging unit 14 is not necessary in all embodiments, and any arrangement or orientation of the imaging unit 14 with respect to the hand-held device 2 is possible provided that the imaging unit 14 is able to obtain images that include identifiable body parts of the subject when the hand-held device 2 is spaced or remote from the subject (i.e. the field of view of the imaging unit 14 should be wide enough or large enough to enable body parts to be visible in the images when the hand-held device 2 is spaced or remote from the subject). For example, a suitable field of view (FOV) could be greater than 30° (equivalent to a 35 mm lens), although higher/wider fields of view are preferred. With a FOV of 30°-40°, the upper arm of a subject will be identifiable from images obtained by the imaging unit 14 when it is a distance of around half the arm length from the arm. Those skilled in the art will be aware of suitable optical arrangements that can provide a field of view of a suitable size.

The imaging unit 14 may include any suitable component for capturing an image, for example a charge-coupled device (CCD) and one or more lenses and/or mirrors. In some embodiments, the imaging unit 14 is a camera, such as a digital camera. In some embodiments, the imaging unit 14 may obtain one or more depth images (or the images obtained by the imaging unit 14 can include depth information), which means that the images contain information about the distances of the parts of the image from the imaging unit 14. Types of imaging unit 14 that can obtain depth images or images with depth information are known to those skilled in the art, for example in the Microsoft Kinect® for the Xbox 360 console.

The displacement sensor 16 is arranged in or on the hand-held device 2 and measures displacement of the hand-held device 2 along the body when the hand-held device 2 is in contact with the body (or clothing). The displacement sensor 16 can therefore be in any suitable position or location in or on the hand-held device 2 that enables the displacement of the hand-held device 2 to be measured when the hand-held device 2 is moved. For example, in the embodiment illustrated in FIG. 1, the displacement sensor 16 is arranged on the head portion 6, close to and generally planar with the aperture 10, so that the displacement sensor 16 will be very close to or in contact with the subject when the head portion 6 is in contact with the subject. The displacement sensor 16 outputs a displacement signal that represents the displacement measured by the displacement sensor 16.

The displacement sensor 16 may be any suitable type of sensor for measuring the displacement of a hand-held device 2 across the body of the subject. For example, the displacement sensor 16 can be an optical-based displacement sensor, such as an optoelectronic sensor, for example as used in optical computer mice. As such, the displacement sensor 16 can include a light source and a light sensor that is responsive to the light from the light source that is reflected from the subject. In these embodiments the displacement signal could be the output of the light sensor, or the displacement signal could be the result of some processing of a signal output by the light sensor (e.g. after the light sensor signal has been filtered to remove noise, etc.).

Finally in FIG. 1, the illustrated hand-held device 2 includes a user control 18 that can be operated by the user to activate the hand-held device 2 and lead to the head portion 6 performing the required operation on the body of the subject (e.g. the generation of an energy pulse by the one or more energy source(s) 12. Alternatively or in addition, the user control 18 can be used by the user to initiate the techniques described herein. The user control 12 may be in the form of a switch, a button, a touch pad, etc.

Figure 2:
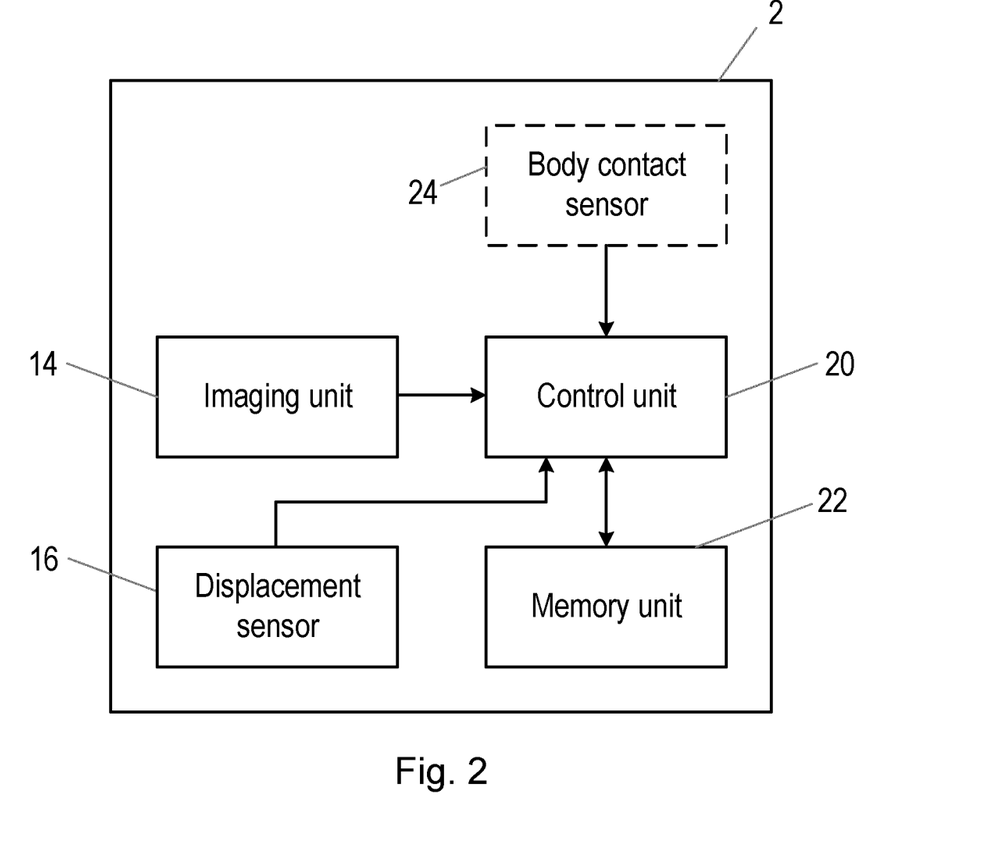
FIG. 2 is a block diagram illustrating exemplary components of a hand-held device according to an embodiment.

FIG. 2 is a block diagram illustrating some components of a handheld device 2 according to an exemplary embodiment.

The hand-held device 2 includes a control unit 20 that is for controlling the operation of the hand-held device 2. The control unit 20 is connected to the imaging unit 14 to receive the images obtained by the imaging unit 14, and connected to the displacement sensor 16 to receive the displacement signal. In some embodiments, the control unit 20 is provided to control to performance of the operation by the head portion 6 (e.g. control the generation of energy pulses, or control activation of a shaving element or hair clipping element). In some embodiments the control unit 20 can also or alternatively process the images from the imaging unit 14 and the displacement signal from the displacement sensor 16 to determine the position and/or orientation of the hand-held device 2 according to the techniques described herein. In embodiments where the control unit 20 does not itself process the images from the imaging unit 14 and the displacement signal from the displacement sensor 16 to determine the position and/or orientation of the hand-held device 2, the control unit 20 can communicate the images and displacement signal to another apparatus for analysis, such as a base unit for the hand-held device 2, a user device such as a smartphone, a smartwatch, a tablet, a laptop or a computer, etc., or a remote device such as a server (e.g. located in the cloud). In these latter embodiments, the hand-held device 2 and the apparatus (e.g. a base unit, a user device such as a smartphone, a smartwatch, a tablet, a laptop or a computer, etc., or remote device) form a system that determines the position and/or orientation of the hand-held device 2.

The control unit 10 (or a processing unit in a separate apparatus) can be implemented in numerous ways, with software and/or hardware, to perform the various functions described herein. The control unit 20 may comprise one or more microprocessors or digital signal processor (DSPs) that may be programmed using software or computer program code to perform the required functions and/or to control components of the control unit 10 to effect the required functions. The control unit 20 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, microcontrollers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The control unit 20 can be connected to a memory unit 22 (or in some embodiments the memory unit 22 can be part of the control unit 20), and the memory unit 22 can store data, information and/or signals for use by the control unit 20 in controlling the operation of the hand-held device 2 and/or in executing or performing the operations to determine the position and/or orientation of the hand-held device 2 described herein. In some implementations the memory unit 22 stores computer-readable code that can be executed by the control unit 20 so that the control unit 20 performs one or more functions, including the operations described herein. The memory unit 22 can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM) and electrically erasable PROM (EEPROM), implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments, the hand-held device 2 may also include a body contact sensor 24 that can measure or detect whether the hand-held device 2, and specifically the head portion 6, is in contact with a body. That is, a body contact sensor 24 can be provided on the hand-held device 2, for example, positioned at or on the head portion 6 so that the body contact sensor 24 is in contact with the body when the hand-held device 2 is in contact with the body, and the body contact sensor 24 outputs a contact signal to the control unit 20 indicating whether there is contact with the body. The body contact sensor 24 can be any suitable type of sensor, for example a pressure sensor, a conductivity sensor, a capacitive contact sensor, a proximity sensor or an optical-based contact sensor (e.g. that can detect contact based on a measured light level). The contact signal may be a voltage signal that varies between high and low voltages (representing contact and no contact between the body contact sensor 24 and the body).

It will be appreciated that a body contact sensor is not required in all embodiments, and in some embodiments it may be possible to determine a contact signal or infer whether there is body contact from the images from the imaging unit 14 (e.g. body contact can be indicated by an obtained image being dark or generally black if the position of the imaging unit 14 on the hand-held device 2 is such that the imaging unit 14 will be generally obscured by the body when the hand-held device 2 is in contact with the body) and/or from the displacement signal from the displacement sensor 16 (e.g. body contact can be indicated by a measurable displacement if the displacement sensor 16 is only able to measure displacement if it is in contact with a surface or body).

It should be noted that FIG. 2 only shows the components of a hand-held device 2 that are useful for implementing the techniques described herein, and a typical hand-held device 2 will include further components. For example the hand-held device 2 may also include a power supply, such as a battery, or components for enabling the hand-held device 2 to be connected to a mains power supply. As another example, the hand-held device 2 can include a user interface that includes one or more components that enables the user to input information, data and/or commands into the hand-held device 2 (including user control 18), and/or enables the hand-held device 2 to output information or data to the user of the hand-held device 2. The user interface can comprise any suitable input component(s), including but not limited to a keyboard, keypad, one or more buttons, switches or dials, a mouse, a track pad, a touchscreen, a stylus, a camera, a microphone, etc., and/or the user interface can comprise any suitable output component(s), including but not limited to a display screen, one or more lights or light elements, one or more loudspeakers, a vibrating element, etc. As yet another example, which can be useful where the hand-held device 2 is required to communicate the obtained images and the displacement signal to an apparatus for processing to determine the position and/or orientation of the hand-held device 2, the hand-held device can include interface circuitry for enabling a data connection to and/or data exchange with other devices, including any one or more of servers, databases, a base unit for the hand-held device 2 and a smartphone or other user device (e.g. computer, laptop, tablet, smartwatch, etc.). The interface circuitry can enable a connection between the hand-held device 2 and another device via any desirable wired or wireless communication protocol.

Briefly, the techniques described herein make use of the images from the imaging unit 14 to provide an absolute position and/or orientation of the hand-held device 2 with respect to a body part of the subject based on recognition of body parts in the images, and use the displacement signal from the displacement sensor 16 to provide a relative position and/or orientation of the hand-held device 2 to a body part once it is close to or in contact with the body of the subject. The images are processed to determine whether a body part of the subject can be identified in the received images, and it is determined whether the hand-held device 2 is in contact with the body. The position and/or orientation of the hand-held device 2 with respect to a body part of the subject is determined according to one of three modes of absolute and relative position and/or orientation tracking in relation to the body part, with the mode to use being selected based on whether the body part can be identified and whether the hand-held device 2 is in contact with the body. This means that the mode of operation to use to determine the position and/or orientation of the hand-held device 2 changes as the hand-held device 2 moves towards, and then contacts, the subject (and likewise changes as the hand-held device 2 is moved away from the subject).

Preferably, both the position of the hand-held device 2 relative to the identified body part and the orientation of the hand-held device 2 with respect to the identified body part are determined, as that provides full information about how the identified body part and hand-held device 2 relate to each other in three dimensions. However, in some embodiments, it is possible to determine only the position or orientation of the hand-held device 2 relative to the identified body part.

In a first mode, which is referred to herein as a 'body-part tracking mode', the hand-held device 2 is distant from the body such that a body part is within the view of the imaging unit 14 and identifiable by analysing the image(s). In this mode, skeleton recognition, body contour mapping, and/or other known or conventional techniques for identifying body parts, can be used to determine the position and/or orientation of the body part relative to the hand-held device 2. In some embodiments, the image analysis to identify body parts can also or alternatively make use of visual features such as markers placed on the subject's body, skin features (e.g. folds/wrinkles, pores, pore density, moles, pigment, etc.) and/or hair distribution (e.g. hair layout patterns). Depending on the body part recognition algorithm or technique used to analyse the images, the whole of a particular body part (e.g. a hand, or a leg) may (or needs to be) visible in the image in order for the body part to be identified and to continue to be identified (although the size of the body part that can be identified (e.g. arm, forearm, hand, finger) will depend on the algorithm or technique. For example, an algorithm or technique may initially identify a body part that is completely visible in an image, and continue to identify that body part in subsequent images based on visual features even when one or more edges of the body part are not visible in those images.

In the first mode, a position of the body part relative to the hand-held device 2 can be determined from the position of the identified body part in the image. The position can be expressed as coordinates (e.g. x-y coordinates), and the coordinates of the centre of the recognized body part in the image are determined (for example a point in the image is set as the origin (e.g. the bottom left hand corner or the centre of the image) and the location coordinates of the centre of the identified body part are determined). The position of the body part relative to the hand-held device 2 is denoted BP_POS. If depth information is available (i.e. information about the distances between the imaging unit 14 and parts of the image), then BP_POS can include a z-component representing the distance between the hand-held device 2 and the identified body part. Alternatively, the z-component can be determined based on scale estimation, which makes use of information on an actual size of the identified body part (e.g. the typical upper arm length is 25 cm, or the specific subject's upper arm length is 23 cm), then it is possible to determine the distance based on the size of the body part in the image.

The orientation of the hand-held device 2 with respect to the body part can be determined as an angle of the hand-held device 2 relative to the identified body part. The orientation of the hand-held device 2 relative to the body part can be determined based on the orientation of the identified body part in the image(s). For example the body part recognition algorithm could provide or identify 3D positions of end points of a body part (such as an arm, arm bone, etc.) and these 3D positions can be used to calculate the orientation of the hand-held device 2 relative to the body part (the 3D positions in this embodiment can be determined using depth information in the image(s)). Optionally, the perspective of skin and/or hair features may provide information about the angle of the hand-held device 2 with respect to the body part. For example, when approaching the body part at an angle under 45°, the features closer to the imaging unit 14 will be larger and the features further from the imaging unit 14 will be smaller. The difference in size between the closer and further points of the body part has a direct relationship to the angle of the hand-held device 2 with respect to the body part, which could be modelled by a function or represented in a look-up table. An advantage of this approach (compared to providing 3D positions) is that the imaging unit 14 does not need to be able to provide depth information. As another example, the angle of the hand-held device 2 can be determined by analysing the relative orientations of visual features of the body part (such as markers, skin features and/or hair layout patterns) in the image(s).

BP_POS and/or the orientation are updated as the hand-held device 2 moves relative to the identified body part. That is, a subsequent image from the imaging unit 14 is analysed as described above to determine the current position of the identified body part in the image, and BP_POS is set as that current position, and/or the current orientation of the identified body part in the image is determined and the orientation is set as that current orientation.

When the (or any) body part is no longer identifiable in the images (e.g. when the edges of the body part are about to go, or have gone, outside the view of the imaging device 14 due to the hand-held device 2 approaching the body and/or certain visual features associated with the body part can no longer be identified), the second mode, which is referred to as an 'off-body tracking mode', is used to determine the position and/or orientation of the body part relative to the hand-held device 2. In this mode, the hand-held device 2 is not yet in contact with the body, but is close enough to the body part that the body part cannot be identified in the received images. In this second mode, techniques such as visual odometry, dead reckoning, feature recognition and tracking (e.g. skin features such as folds/wrinkles, pores, pore density, moles, pigment, etc., and/or hair distribution (e.g. hair layout patterns) and/or pixel density can be used to determine the position and/or orientation of the hand-held device 2 relative to the body part, with the last updated BP_POS being used as the starting point for determining the current position (the last updated BP_POS will be the position of the hand-held device 2 relative to the identified body part at the last point where the body part can be identified in the images) and the last updated orientation in the first mode being used as the starting point for determining the current orientation.

As is known in the art, visual odometry is a process of determining movement using several (preferably sequential) images to estimate a distance traveled. Dead reckoning techniques are also known in the art, and is a process by which a current position is calculated by using a previously determined position, or fix, and updating that position based upon known or estimated speeds of movement over time and the direction of that movement.

The position of the hand-held device 2 relative to the body part determined according to the second mode is denoted SK2_POS (e.g. SK2_POS=BP_POS+Δposition2, where Δposition2 is the change in the position measured during the second mode). In some embodiments, SK2_POS can be calculated based on scale, orientation and motion in relation to recognised skin and/or hair features. In the second mode a change in orientation of the hand-held device 2 relative to the body part can be determined, and the orientation can be given by applying the determined change in orientation during the second mode to the last determined orientation in the first mode.

When the hand-held device 2 touches or contacts the body (e.g. contacts or touches skin or clothing), the third mode, which is referred to as an 'on-body tracking mode' is used to determine the position of the body part relative to the hand-held device 2. In this mode, the displacement signal is analysed or processed to determine an amount of displacement (e.g. planar displacement) along the body. The amount of displacement can be determined from the displacement signal using conventional techniques for analysing displacement signals (e.g. conventional techniques for determining an amount and direction of displacement using an optical displacement sensor). This amount of displacement can be used to determine the position of the hand-held device 2 relative to the body part, with the last updated SK2_POS being used as the starting point for determining the current position (the last updated SK2_POS will be the position of the hand-held device 2 relative to the body part at the point where the hand-held device 2 contacted or touched the skin or clothing of the subject). The position of the hand-held device 2 relative to the body part determined according to the third mode is denoted SK3_POS, and can be given by SK3_POS=SK2_POS+Δposition3, where Δposition3 is the displacement measured during the third mode.

Figure 3:
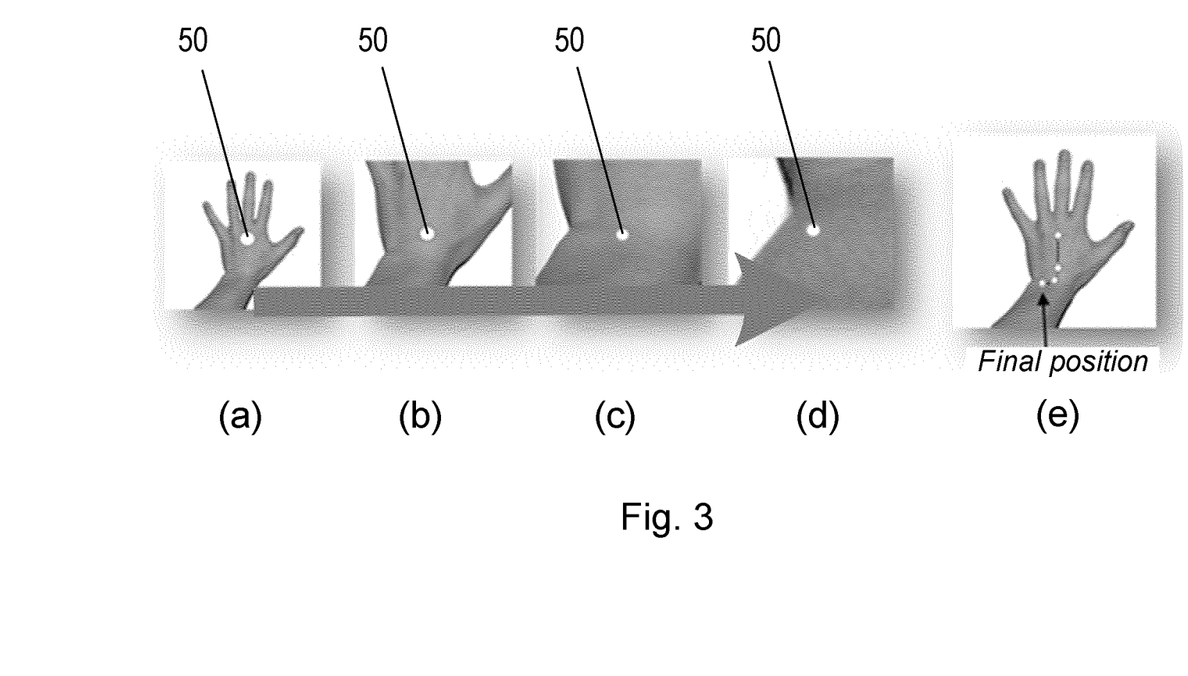
FIG. 3 is an exemplary series of images obtained by an imaging unit as a hand-held device is moved towards a hand of a subject.

FIG. 3 is an exemplary series of images obtained by an imaging unit 14 as a hand-held device 2 is moved towards a hand of a subject. In FIG. 3(*a*) a hand can be identified, and a point 50 on the hand is identified that the hand-held device 2 is moving towards. At this stage the position and/or orientation of the hand-held device 2 relative to the subject is determined using the first mode (the body tracking mode). FIGS. 3(*b*)-(*d*) show the hand-held device 2 approaching the hand, with the hand no longer identifiable in the images shown in FIGS. 3(*c*) and (*d*) (at least—it is possible that it may not be possible to identify the body part in FIG. 3(*b*) as well). During this movement (FIGS. 3(*b*)-(*d*)), as the body part is no longer identifiable but the hand-held device 2 is not in contact with the subject, the position and/or orientation of the hand-held device 2 relative to the subject is determined using the second mode (the off-body tracking mode). Each of FIGS. 3(*b*)-(*d*) show the point 50 on the hand that the hand-held device 2 is moving towards, and it can be seen that the position of the point 50 on the hand is refined as the hand-held device 2 moves towards the hand. FIG. 3(*e*) is an image of the hand showing how the position of the point 50 is refined as the hand-held device 2 is moved towards the hand.

Figure 4:
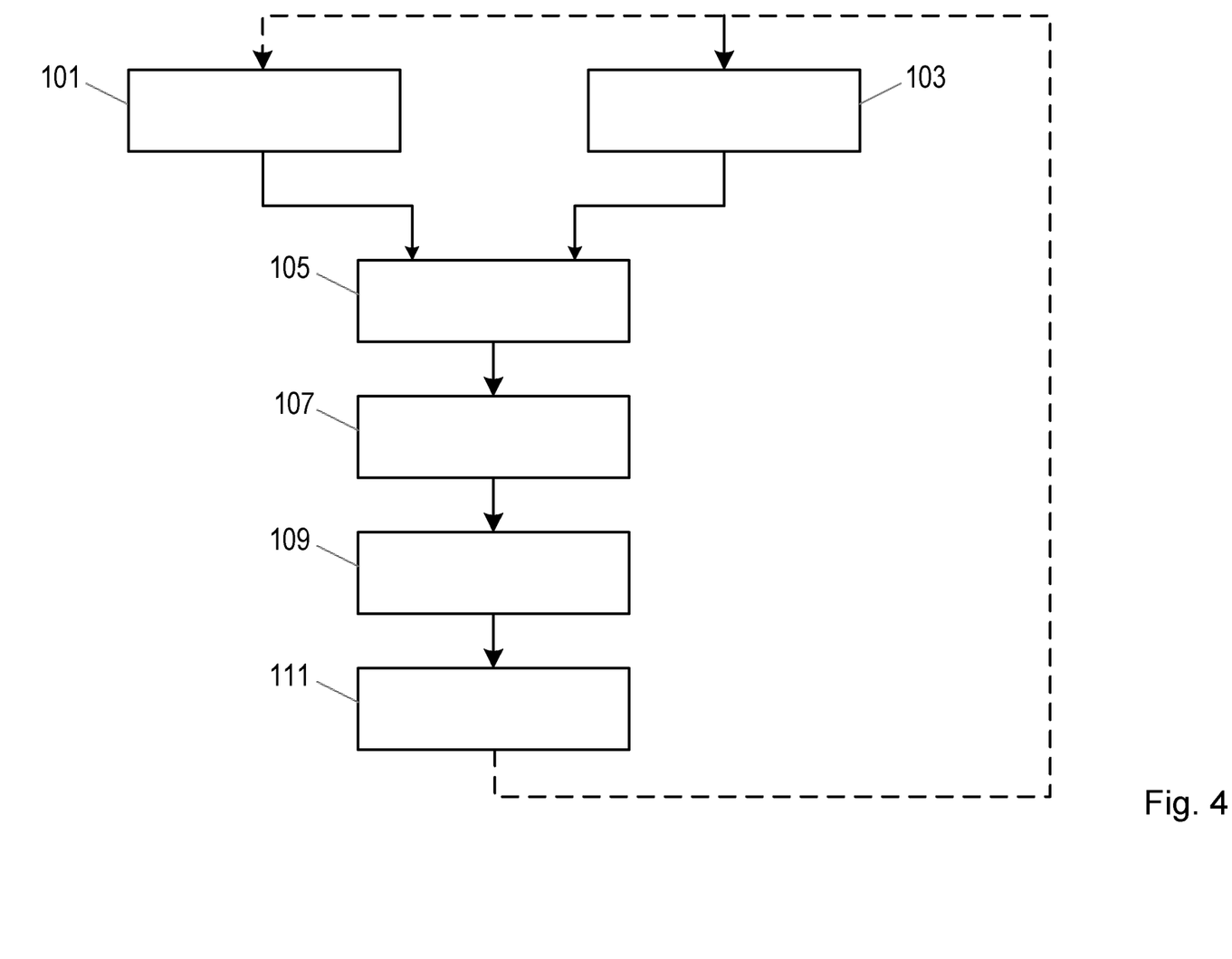
FIG. 4 is a flow chart illustrating a method according to an exemplary embodiment.

The flow chart in FIG. 4 illustrates an exemplary method according to the techniques described herein. One or more of the steps of the method can be performed by the control unit 20 in the hand-held device 2, in conjunction with any of the memory unit 22, imaging unit 14 and displacement sensor 16 as appropriate. The control unit 20 may perform the one or more steps in response to executing computer program code, that can be stored on a computer readable medium, such as, for example, the memory unit 22. Alternatively, one or more of the steps of the method can be performed by a processing unit or control unit associated with or part of an apparatus (e.g. a smartphone, tablet, etc.) that is separate from the hand-held device 2. That apparatus may also perform the one or more steps in response to executing computer program code that can be stored on a computer readable medium.

In step 101, a series of images are received from the imaging unit 14. In step 103, a displacement signal is received from the displacement sensor 16. Steps 101 and 103 can be performed at the same time or at substantially the same time. Preferably, the images received in step 101 and the displacement signal received in step 103 are received in real-time (i.e. as the images and displacement signal are generated) or near-real-time (i.e. within a short time period of the images and displacement signal being generated, e.g. less than 1 second). This enables the position and/or orientation of the hand-held device 2 relative to the body part to be determined in real-time or near-real-time as appropriate.

Next, in step 105, the received images are processed to determine whether a body part of the subject can be identified in the received images. There are numerous image analysis techniques available that are able to identify body parts in an image or a series of images, and those skilled in the art will be aware of suitable techniques that can be used in step 105. For example, techniques are available that can recognise parts of the human or animal skeleton in the image (e.g. similar to the techniques used in the Microsoft® Kinect® device). Another suitable technique which can be used in addition to or as an alternative to skeleton recognition is body contour mapping, for example as described in "An Efficient Human Body Contour Extraction Method for Mobile Apps" by Wang et. al, http://eprints-.bournemouth.ac.uk/29341/1/edu-wang.pdf. Other techniques can identify body parts by identifying visual features on the body part (including markers, skin features, etc.).

The type of body part that can be detected in step 105 can depend on the type of image analysis technique being used. However, in general step 105 can comprise processing the received images to attempt to identify one or more major (i.e. larger) body parts such as the torso, chest, back, head, limbs (one or both arms, one or both legs), etc. In some embodiments, step 105 can comprise processing the received images to attempt to identify one or more minor (i.e. smaller) body parts, such as the face, ears, hand, forearm, wrist, thigh, knee, foot, etc.

In step 107, it is determined whether the hand-held device 2 is in contact with the body. In embodiments where the hand-held device 2 includes a body contact sensor 24, step 107 can comprise or include determining whether the contact signal output by the body contact sensor 24 indicates that there is contact with the body (including contact with clothing, if a suitable body contact sensor 24 is being used). As noted above, if the position of the imaging unit 14 on the hand-held device 2 is such that the imaging unit 14 will be generally obscured when the hand-held device 2 is in contact with the body, it is also possible to determine whether the hand-held device 2 is in contact with the body in step 107 by analysing the received images. In particular, if the received image is dark or generally black (e.g. if an average brightness level of the image is below a threshold), it could be inferred that the hand-held device 2 is in contact with the body. It will be appreciated that this image analysis technique could be used as an alternative to, or in combination with, the use of body contact sensor 24. Also as noted above, if the displacement sensor 16 is only able to measure displacement if it is in contact with a surface or body, it is also possible to determine whether the hand-held device 2 is in contact with the body in step 107 by analysing the displacement signal. In particular, if the displacement signal indicates that there is a non-zero displacement or a displacement above a threshold it could be inferred that the hand-held device 2 is in contact with the body. It will be appreciated that the use of the displacement signal in this way can be an alternative to, or used in combination with, the use of body contact sensor 24 and/or the 'dark images'.

It will be appreciated that although steps 105 and 107 are shown as being sequential in FIG. 4, they can be performed at generally the same time, or in the opposite order. It will also be appreciated from the following explanation that, as a body part is typically only identifiable in the received images when the hand-held device 2 is spaced or distant from the body, if a body part is identified step 105, it may not be necessary to perform step 107 at that point as it can be assumed that the hand-held device 2 is not in contact with the body. In this case, as noted below with reference to step 109, it can be determined in step 109 that the first mode should be used to determine the position and/or orientation of the identified body part relative to the hand-held device 2 just based on the image analysis in step 105. Likewise, if step 107 is performed before step 105 and it is determined that the hand-held device 2 is in contact with the body it may not be necessary to perform step 105 at that point as it can be assumed that a body part will not be identifiable in images from the imaging unit 14. In this case, as noted below with reference to step 109, it can be determined in step 109 that the third mode should be used to determine the position and/or orientation of the identified body part relative to the hand-held device 2 just based on the body contact detection in step 107.

In step 109, a mode of operation to use to determine a position and/or orientation of the hand-held device 2 with respect to the body of the subject is determined based on whether a body part can be identified and whether the hand-held device 2 is in contact with the body.

In particular, in step 109 it is determined that the first mode of operation should be used when a body part can be identified in the images in step 105. It is determined that the second mode of operation should be used when a body part cannot be identified in the received images in step 105 and it is determined in step 107 that the hand-held device 2 is not in contact with the body. It is determined that the third mode of operation should be used when it is determined in step 107 that the hand-held device 2 is in contact with the body.

Next, in step 111, the position and/or orientation of the hand-held device 2 with respect to the body of the subject is determined using the received images and/or received displacement signal according to the mode of operation determined in step 109.

As noted above, when operating in the first mode, step 111 comprises processing the received images to determine a first position (BP_POS) and/or first orientation of the hand-held device 2 with respect to the body part identified in the received images.

When operating in the second mode, step 111 comprises processing the received images to determine an amount of movement of the hand-held device 2 from the determined first position (BP_POS) and/or an amount of change in the orientation of the hand-held device 2 from the determined first orientation. This results in a second position (SK2_POS) of the hand-held device 2 with respect to the identified body part, which is determined from the first position (BP_POS) and the determined amount of movement. This can also result in a second orientation of the hand-held device 2 with respect to the identified body part, which is based on the determined first orientation and the determined amount of change.

When operating in the third mode, step 111 comprises processing the received displacement signal to determine an amount of displacement of the hand-held device 2 along the body from the determined second position (SK2_POS). This results in a third position (SK3_POS) of the hand-held device 2 with respect to the identified body part from the determined second position (SK2_POS) and the determined amount of displacement.

Once the position and/or orientation of the hand-held device 2 has been determined in step 111, the method can return to steps 101 and 103 and repeat for a new image or set of images and a new displacement signal to determine an updated position of the hand-held device 2.

It will be appreciated that after determining an initial mode of operation to use in step 111 based on the outcomes of step 105 and step 107, the method can continue to use that mode to determine the position and/or orientation of the body part with respect to the hand-held device 2 until the outcomes of step 105 and/or step 107 change. Thus, the first mode of operation will be used until it is no longer possible to identify the body part in the received images, at which point the outcome of step 105 will change to 'no body part detected', and the mode of operation will change to the second mode. Likewise, the second mode of operation will be used until either (i) a body part is identifiable in the received images, at which point the outcome of step 105 will change to 'body part detected', and the mode of operation will change to the first mode, or (ii) the hand-held device 2 is in contact with the body, at which point the outcome of step 107 will change to 'body contact detected', and the mode of operation will change to the third mode. The third mode of operation will be used until either (i) a body part is identifiable in the received images, at which point the outcome of step 105 will change to 'body part detected' and the outcome of step 107 will change to 'no body contact detected', and the mode of operation will change to the first mode, or (ii) no body part is identifiable in the received images, but the outcome of step 107 changes to 'no body contact detected', and the mode of operation will change to the second mode.

While operating in the first mode, repeating step 111 on newly received images and a newly received displacement signal will result in updates to the first position (BP_POS) and/or first orientation over time. When the mode of operation changes to the second mode, the second mode bases the second position (SK2_POS) on the last updated first position (last updated BP_POS) and the second orientation on the last updated first orientation. Likewise, while operating in the second mode, repeating step 111 on newly received images and a newly received displacement signal will result in updates to the second position (SK2_POS) and/or second orientation over time. When the mode of operation changes to the third mode, the third mode bases the third position (SK3_POS) on the last updated second position (last updated SK2_POS). While operating in the third mode, repeating step 111 on newly received images and a newly received displacement signal will result in updates to the third position over time.

The position and/or orientation determined in step 111 can be used in a number of possible ways. In particular, the position and/or orientation can be used by the control unit 20 (in which case if the position and/or orientation is determined by a device other than the hand-held device 2, the position and/or orientation determined in step 111 is provided to the control unit 20). In some embodiments, the determined position and/or orientation can be used to determine whether the operation or treatment operation can be performed by the head portion 6. For example, it may be that the operation (e.g. energy pulses for photoepilation) can only be performed when the head portion 6 is in contact with the body, in which case if the determined position and/or orientation indicates that the hand-held device 2 is not in contact with the body, the operation by the head portion 6 may be prevented. For example, it may be that the operation (e.g. energy pulses for photoepilation) can only be performed when the head portion 6 is in contact with the body, in which case if the determined position and/or orientation indicates that the hand-held device 2 is not in contact with the body, the operation by the head portion 6 may be prevented. In some embodiments, it may be that the operation or treatment operation can or should only be performed on certain body parts (e.g. the legs), or certain parts of body parts (e.g. skin, and not nails), and information on these 'permitted' or 'prohibited' parts of the body and the determined position and/or orientation can be used to determine whether the operation or treatment operation can be performed at the position of the hand-held device 2. In some embodiments, the control unit 20 may store information on the positions of the hand-held device 2 on the body part where previous operations have been performed, and the control unit 20 can permit the performance of the operation if the hand-held device 2 is at a new position (i.e. a position where the operation has not yet been performed). These embodiments can help to prevent over treatment of parts of the body, and improve the coverage of the treatment on the body part. In some embodiments, it may be that the operation or treatment operation can have different settings depending on the part of the body that the operation or treatment operation is performed on, in which case the control unit 20 can adjust the settings of the operation or treatment operation based on the determined position (and thus based on the body part to be treated). Separate from or in conjunction with any of the previous embodiments, the control unit 20 can use the determined position and/or orientation to provide directions and/or guidance to the user to move the hand-held device 2 to an appropriate or desired position at which the operation can be performed (including adjusting the orientation of the hand-held device 2). These directions and/or guidance can be provided via a user interface on the hand-held device 2.

Figure 5:
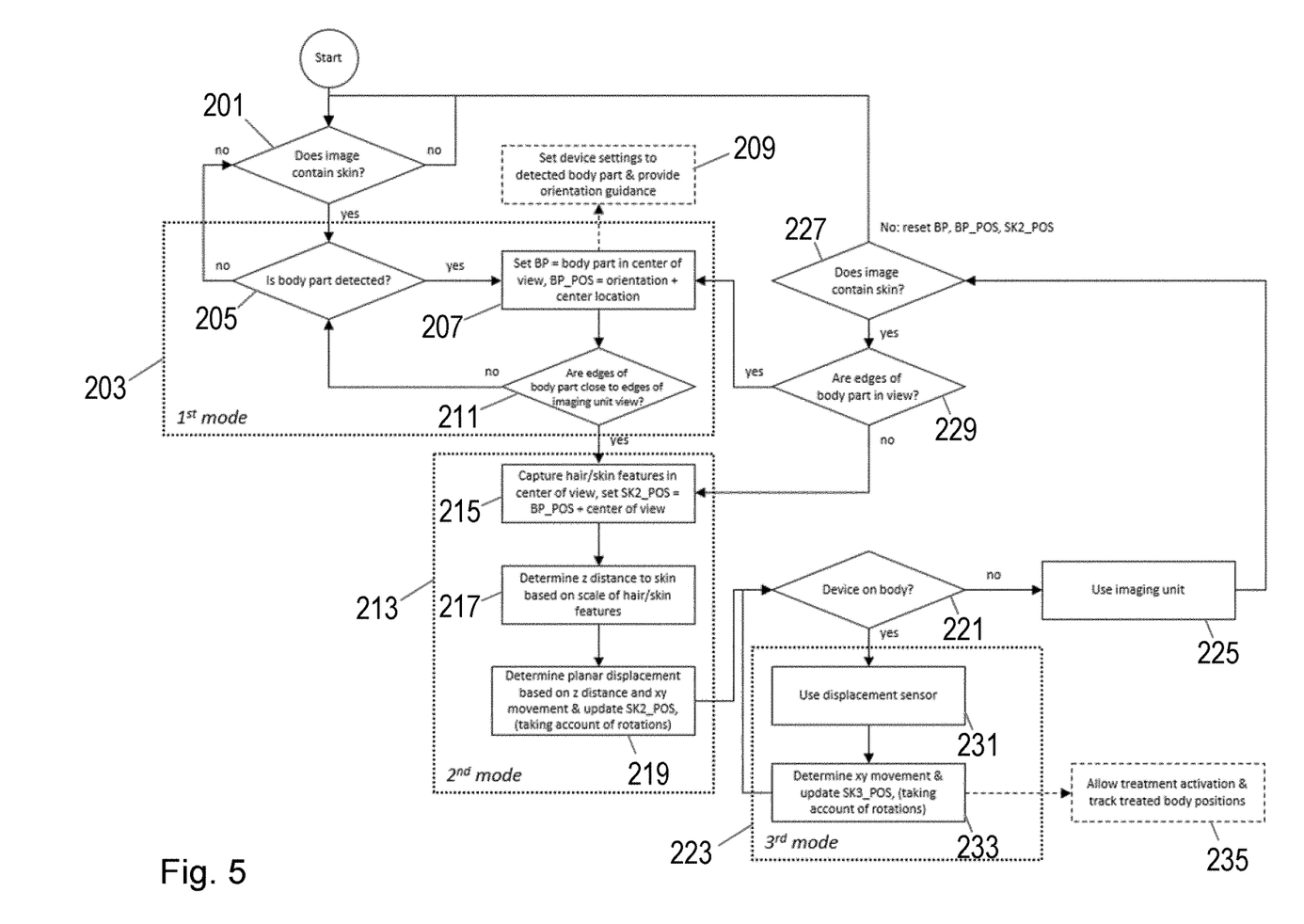
FIG. 5 is a flow chart illustrating a decision flow and method steps according to an exemplary embodiment.

The flow chart in FIG. 5 illustrates a method of determining the position and orientation of a body part with respect to the hand-held device 2 according to the various modes set out above. At the start of the method, it is assumed that the hand-held device 2 is distant from the body.

The method starts with step 201 (which is an optional step), in which it is determined whether the received image(s) contain or include skin (e.g. the images received according to step 101). This step can use known algorithms or techniques for detecting skin in images, for example as described in "Comparison of pixel based skin recognition techniques" by Borislav Banchev and Lidiya Georgieva (found at http://conf.uni-ruse.bg/bg/docs/cp12/3.2/3.2-30.pdf). For example, the images can be analysed using remote photoplethysmogram (rPPG) techniques to determine if there is any part of the image exhibiting pulsations (e.g. changes in brightness) consistent with a heart rate. If no skin is detected in the image(s), the method repeats step 201 for the next received image(s).

If skin is detected in step 201, the position of the hand-held device 2 is determined using the first mode of operation, which is set out in box 203. Thus, in step 205, it is determined if a body part is detectable or identifiable in the image(s) that contain skin. Step 205 can be performed in the same way as step 105 above, for example using skeleton recognition, body contour mapping and/or other techniques (e.g. based on visual features) to identify body parts. If no body part is detected or identified in step 205, the method returns to step 201 and repeats for the next received image(s).

If a body part is detected in the image(s), then the method passes to step 207. In step 207 the identified body part, BP, is set as the body part in the centre of the image (view) and the position of the identified body part relative to the hand-held device 2 (BP_POS) is set as the position of the identified body part at the centre location (or other designated origin point) of the image (which is expressed as xy coordinates).

Optionally, in step 209, one or more settings (e.g. operation settings or treatment settings) of the hand-held device 2 can be adjusted based on the identified body part, and/or guidance can be provided to the user of the hand-held device 2 based on the identified body part and BP_POS. In some embodiments, the guidance can include adjustments to the orientation of the hand-held device 2 so that it is better aligned with the body part (e.g. so that the hand-held device 2 is approaching the body part perpendicular to the skin).

After step 207, the method checks in step 211 whether edges of the identified body part are close to the edges of the view of the imaging unit 14 (i.e. close to the edges of the images). Depending on the algorithm or technique being used, this step can correspond to determining if it is still possible to identify the body part in the image. Alternatively, this step can analyse the image to determine a distance between the edge of the body part and the edge of the image using known image analysis techniques. If the edges are not close to the images/imaging unit 14 view (i.e. the body part is still identifiable), the method remains in the first mode 203 and returns to step 205 to check whether the body part is still detected in the next image or images. If so, the method repeats step 207 to update BP_POS.

If in step 211 it is determined that the edges of the body part are close to the edges of the image (i.e. it might not be possible to identify the body part in the images any longer), the method switches to the second mode as set out in box 213.

In step 215 of the second mode, hair and/or skin features of the body part in the view (image) are identified, for example using conventional image analysis techniques. This also involves identifying the position of the hair and/or skin features in the image. Step 215 may comprise identifying hair and/or skin features of the body part in the centre of the body part in the view. Initially in the second mode, the position of the body part relative to the hand-held device 2 (denoted SK2_POS) is set to be the last updated BP_POS in the first mode, as measured from the relevant 'origin' point in the image (e.g. the bottom left hand corner or the centre of the image).

Next, in step 217 (which is optional) a distance z (or a change in distance z while in the second mode) is determined that represents the distance from the hand-held device 2 to the skin. In some embodiments, this distance z or change in distance z can be determined based on identifying hair and/or skin features in the image, and determining the scale and/or relative size of these features in the image. The distance z or change in distance z can be derived based on the scale and/or relative size of these features (e.g. the larger the feature, the closer the hand-held device 2 is to the feature on the skin). In addition or alternatively, this step can use visual odometry techniques to determine the distance z or change in distance z. The position of the body part relative to the hand-held device 2 is updated based on the determined distance z or change in distance z.

Next, in step 219, a planar displacement (xy) of the body part relative to the hand-held device 2 while in the second mode is determined. This step determines the distance that the skin/hair features identified in step 215 have moved in the image relative to their position(s) at the start of the second mode. This step can use techniques such as visual odometry and/or dead reckoning to determine the distance that the skin/hair features have moved. Alternatively this step can use pixel density to determine the amount of movement of the skin/hair features from the last BP_POS and/or a change in orientation of the hand-held device 2. The position SK2_POS is then updated based on the planar displacement (i.e. 'updated SK2_POS'=final BP_POS)+'planar displacement while in the second mode'). A change in orientation of the hand-held device 2 relative to the body part can also be determined in step 219, for example based on rotation of the positions of the identified skin/hair features in the image relative to the positions of the skin/hair features as identified in step 215.

In the second mode 213, it is checked whether the hand-held device 2 is in contact with the body (i.e. clothing or skin) in step 221. Step 221 can be performed in a similar way to step 107. If in step 221 it is determined that the hand-held device 2 is in contact with the body, then the method switches to determining the position of the hand-held device 2 relative to the body part using the third mode of operation, which is set out in box 223. However, if in step 221 it is determined that the hand-held device 2 is not in contact with the body, the method passes to step 225 where one or more further images are obtained. Optionally, these image(s) are checked to determine if the image(s) contain or include skin (step 227), which is similar to step 201 above.

If at step 227 the image(s) are found not to contain skin, the position of the hand-held device 2 relative to the body part (BP_POS, SK2_POS and/or SK3_POS) are reset, and the method returns to step 201 (or step 205 if step 201 is omitted) and awaits the next image(s).

If at step 227 the image(s) are found to contain skin, or if step 227 is omitted, the method passes to step 229 in which it is determined if the edges of a body part are in view. Step 229 is performed in a similar way to step 211.

If edges of the body part are in view, the method returns to step 207 in the first mode 203 and repeats for the images received in step 225 to update the position of the hand-held device 2 relative to the body part.

If edges of the body part are not in view, the method returns to step 215 in the second mode 213 and repeats for the images received in step 225 to update the position of the hand-held device 2 relative to the body part.

It should be noted that although steps 221-229 are not shown as being inside the second mode box 213, these steps are performed while operating in the second mode.

In the third mode 223 (entered after detecting that the hand-held device 2 is in contact with the body in step 221), the signal from the displacement sensor 16 is obtained (step 231) and analysed in step 233 to determine the displacement (as an xy movement), and the position of the hand-held device 2 (SK3_POS) is updated based on the displacement. Changes in orientation of the hand-held device 2 can also be detected and the orientation of the hand-held device 2 updated.

Optionally, now that the hand-held device 2 is in contact with the body and the position of the hand-held device 2 is known, the position can be used to, for example, determine whether the head portion 6 can perform the operation or treatment operation and/or the determined position can be used to tracked the positions on the body that have been operated on or treated (step 235).

The third mode 223 continues to be used to determine the position of the hand-held device 2 while the hand-held device 2 remains in contact with the body (as determined in step 221).

Therefore, there are provided improvements in the way in which a position of a hand-held device with respect to the body of a subject that does not require any sensors or devices external to the hand-held device to capture information required for determining the position, and that enables a position to be determined when the hand-held device is both remote from the body part and in contact with the body part.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining a position of a hand-held device with respect to a subject, wherein the hand-held device is for use on a body of the subject, the method comprising
receiving images from an imaging unit, wherein the imaging unit is arranged in or on the hand-held device;
receiving a displacement signal from a displacement sensor, wherein the displacement sensor is arranged in or on the hand-held device to measure displacement of the hand-held device along the body when the hand-held device is in contact with the body;
processing the received images to determine whether a body part of the subject can be identified in the received images;
determining whether the hand-held device is in contact with the body;
determining a mode of operation to use to determine a position of the hand-held device based on whether the body part can be identified and whether the hand-held device is in contact with the body; wherein the mode of operation to use is determined as a first mode when the body part can be identified as an identified body part, a second mode when the body part cannot be identified and the hand-held device is not in contact with the body, and a third mode when the hand-held device is in contact with the body; and
determining the position of the hand-held device with respect to the body of the subject using at least one of the received images or received displacement signal according to the determined mode of operation;
wherein, when operating in the first mode, the determining the position of the hand-held device comprises processing the received images to determine a first position of the hand-held device with respect to the identified body part;
wherein, when operating in the second mode, the determining the position of the hand-held device comprises processing the received images to determine an amount of movement of the hand-held device from the determined first position, and determining a second position of the hand-held device with respect to the identified body part from the determined first position and the determined amount of movement, and
wherein, when operating in the third mode, the determining the position of the hand-held device comprises processing the received displacement signal to determine an amount of displacement of the hand-held device along the body from the determined second position, and determining a third position of the hand-held device with respect to the identified body part from the determined second position and the determined amount of displacement.

2. The method according to claim 1, wherein the determining the position of the hand-held device with respect to the body of the subject using at least one of the received images or received displacement signal according to the determined mode of operation also comprises determining an orientation of the hand-held device and;
wherein the method when operating in the first mode comprises processing the received images to determine a first orientation of the hand-held device with respect to the identified body part and;
wherein when operating in the second mode, the determining the orientation of the hand-held device comprises processing the received images to determine an amount of change in orientation of the hand-held device from the determined first orientation and determining a second orientation of the hand-held device with respect to the identified body part from the determined first orientation and the determined amount of change.

3. The method as defined in claim 2, wherein in the third mode the determining the orientation comprises processing subsequent images received from the imaging unit in order to determine a change in orientation from an image transformation between the subsequent images and determining a third orientation of the hand-held device with respect to the identified body part from the determined second orientation and the determined amount of change from the image transformation.

4. The method as defined in claim 2,
wherein, when operating in the second mode, the second orientation is determined from a last first orientation determined when last operating in the first mode.

5. The method as defined in claim 4,
wherein, when operating in the second mode, the second position is determined from a last first position determined when last operating in the first mode.

6. The method as defined in claim 1, wherein, if the position or position and orientation of the hand-held device is determined using the first mode, the method further comprises:
if the body part can be identified in further received images, continuing to operate in the first mode to determine the position or position and orientation of the hand-held device with respect to the body using the further received images; and
if the body part cannot be identified in the further received images, operating in the second mode to determine the position or position and orientation of the hand-held device with respect to the body using the further received images.

7. The method as defined in claim 1, wherein, if at least one of the position or orientation of the hand-held device is determined using the second mode, the method further comprises:
if the body part cannot be identified in further received images and the hand-held device is not in contact with the body, continuing to operate in the second mode to determine the position or position and orientation of the hand-held device with respect to the body using the further received images;
if the body part can be identified in the further received images, operating in the first mode to determine the position or position and orientation of the hand-held device with respect to the body using the further received images; and
if the hand-held device is in contact with the body, operating in the third mode to determine the position or position and orientation of the hand-held device with respect to the body using a further received displacement signal.

8. The method as defined in claim 1, wherein, if the position or position and orientation of the hand-held device is determined using the third mode, the method further comprises:
if the hand-held device is in contact with the body, continuing to operate in the third mode to determine the position or position and orientation of the hand-held device with respect to the body using a further received displacement signal;
if the hand-held device is not in contact with the body and the body part cannot be identified in further received images, operating in the second mode to determine the position or position and orientation of the hand-held device with respect to the body using the further received images; and
if the hand-held device is not in contact with the body and the body part can be identified in the further received images, operating in the first mode to determine the position or position and orientation of the hand-held device with respect to the body using the further received images.

9. The method as defined in claim 1, wherein, when operating in the second mode, the second position is determined from a last first position determined when last operating in the first mode.

10. The method as defined in claim 1, wherein, when operating in the third mode, the third position is determined from a last second position determined when last operating in the second mode.

11. The method as defined in claim 1, wherein the determining whether the hand-held device is in contact with the body comprises:
receiving a contact signal from a body contact sensor; and
processing the contact signal to determine whether the hand-held device is in contact with the body.

12. The method as defined in claim 1, wherein the determining whether the hand-held device is in contact with the body comprises at least one of:
determining whether the hand-held device is in contact with the body by analysing the received images, or
determining whether the hand-held device is in contact with the body by analysing the received displacement signal.

13. The method as defined in claim 1, wherein the method further comprises:
controlling or adjusting control of the hand-held device based on the determined third position.

14. A computer program product comprising a non-transitory computer readable medium having computer readable code embodied therein, the computer readable code being configured such that, on execution by a suitable processing unit or control unit, the processing unit or control unit is caused to perform the method of claim 1.

15. An apparatus for use in determining, with respect to a subject, at least one of a position or orientation of a hand-held device configured for use on a body of the subject, the apparatus comprising a processing unit or a control unit configured to:
receive images from an imaging unit, wherein the imaging unit is arranged in or on the hand-held device;
receive a displacement signal from a displacement sensor, wherein the displacement sensor is arranged in or on the hand-held device to measure displacement of the hand-held device along the body when the hand-held device is in contact with the body;
process the received images to determine whether a body part of the subject can be identified in the received images;
determine whether the hand-held device is in contact with the body;
determine a mode of operation to use to determine a position of the hand-held device based on whether the body part can be identified and whether the hand-held device is in contact with the body; wherein the mode of operation to use is determined as a first mode when the body part can be identified as an identified body part a second mode when the body part cannot be identified and the hand-held device is not in contact with the body, and a third mode when the hand-held device is in contact with the body; and
determine the position of the hand-held device with respect to the body of the subject using at least one of the received images or received displacement signal according to the determined mode of operation;
wherein, when operating in the first mode, determining the position of the hand-held device comprises processing the received images to determine a first position of the hand-held device with respect to the identified body part;

wherein, when operating in the second mode, determining the position of the hand-held device comprises processing the received images to determine an amount of movement of the hand-held device from the determined first position, and determining a second position of the hand-held device with respect to the identified body part from the determined first position and the determined amount of movement; and wherein, when operating in the third mode, determining the position of the hand-held device comprises processing the received displacement signal to determine an amount of displacement of the hand-held device along the body from the determined second position, and determining a third position of the hand-held device with respect to the identified body part from the determined second position and the determined amount of displacement.

16. An apparatus as claimed in claim 15, wherein the hand-held device comprises:
   a treatment head portion for performing a treatment operation on the body of the subject.

17. A system for use in determining a position or position and orientation of a hand-held device with respect to a subject, the system comprising:
   a hand-held device that comprises an imaging unit arranged in or on the hand-held device and a displacement sensor arranged in or on the hand-held device; and
   an apparatus as claimed in claim 15.

* * * * *